(12) United States Patent  (10) Patent No.: US 8,676,347 B2
Finley et al.  (45) Date of Patent: Mar. 18, 2014

(54) BRAIDED LEAD WITH EMBEDDED FIXATION STRUCTURES

(75) Inventors: James Finley, Minneapolis, MN (US); John Swoyer, Blaine, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/537,494

(22) Filed: Jun. 29, 2012

(65) Prior Publication Data

US 2014/0005754 A1    Jan. 2, 2014

(51) Int. Cl.
*A61N 1/05* (2006.01)

(52) U.S. Cl.
USPC .......................................................... 607/117

(58) Field of Classification Search
USPC ............................... 607/2, 116–117, 126–128
See application file for complete search history.

(56) References Cited

U.S. PATENT DOCUMENTS

| | | | | |
|---|---|---|---|---|
| 4,744,371 A * | 5/1988 | Harris | ............................ | 607/117 |
| 5,619,903 A * | 4/1997 | Rogers et al. | ........................ | 87/7 |
| 6,090,104 A * | 7/2000 | Webster, Jr. | .................... | 606/41 |
| 2002/0177888 A1 | 11/2002 | Williams et al. | | |
| 2007/0255369 A1 * | 11/2007 | Bonde et al. | ................... | 607/116 |
| 2008/0183257 A1 * | 7/2008 | Imran et al. | .................... | 607/117 |
| 2008/0183263 A1 | 7/2008 | Alexander | | |
| 2009/0210043 A1 * | 8/2009 | Reddy | ............................ | 607/127 |
| 2010/0137928 A1 | 6/2010 | Duncan et al. | | |
| 2011/0054581 A1 | 3/2011 | Desai et al. | | |
| 2011/0054584 A1 | 3/2011 | Alexander et al. | | |
| 2011/0160830 A1 | 6/2011 | Morris et al. | | |
| 2011/0218603 A1 | 9/2011 | Victorine et al. | | |
| 2012/0035616 A1 | 2/2012 | Olsen et al. | | |

* cited by examiner

*Primary Examiner* — Carl H Layno
*Assistant Examiner* — Paula J Stice
(74) *Attorney, Agent, or Firm* — Michael P. Horvath

(57) ABSTRACT

A therapy delivery element including a plurality of fibers braided to form an elongated braided structure with a lumen. At least one reinforcing structure is woven into the fibers of the braided structure. A portion of at least one reinforcing structure extends from the braided structure to form a fixation structure. A conductor assembly including a plurality of conductors is located in the lumen. An electrode assembly is located at a distal end of the conductor assembly. The electrode assembly includes a plurality of electrodes that are electrically coupled to the conductors. A connector assembly is located at a proximal end of the conductor assembly. The connector assembly includes a plurality of electrical contacts that are electrically coupled to the conductors. At least one of the braided structure or the reinforcing structure is attached to at least one of the electrode assembly or the connector assembly.

22 Claims, 16 Drawing Sheets

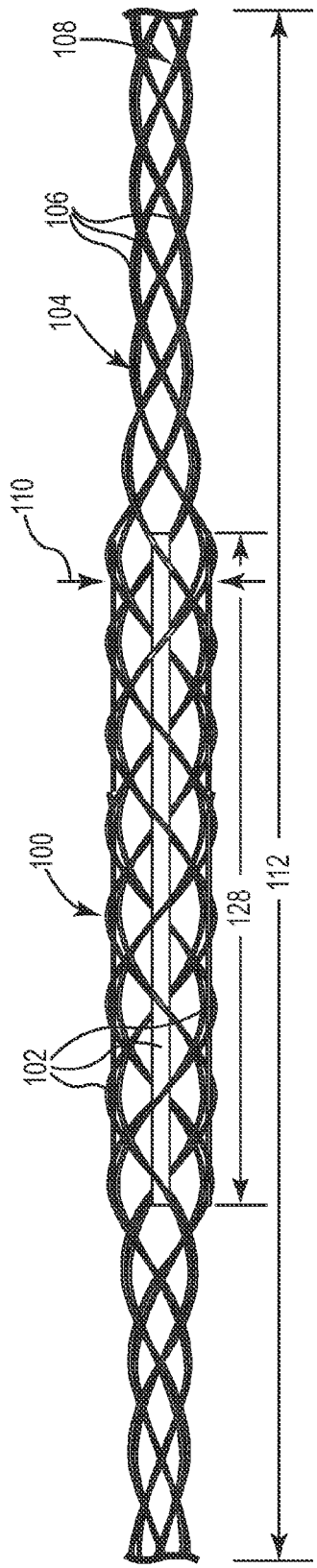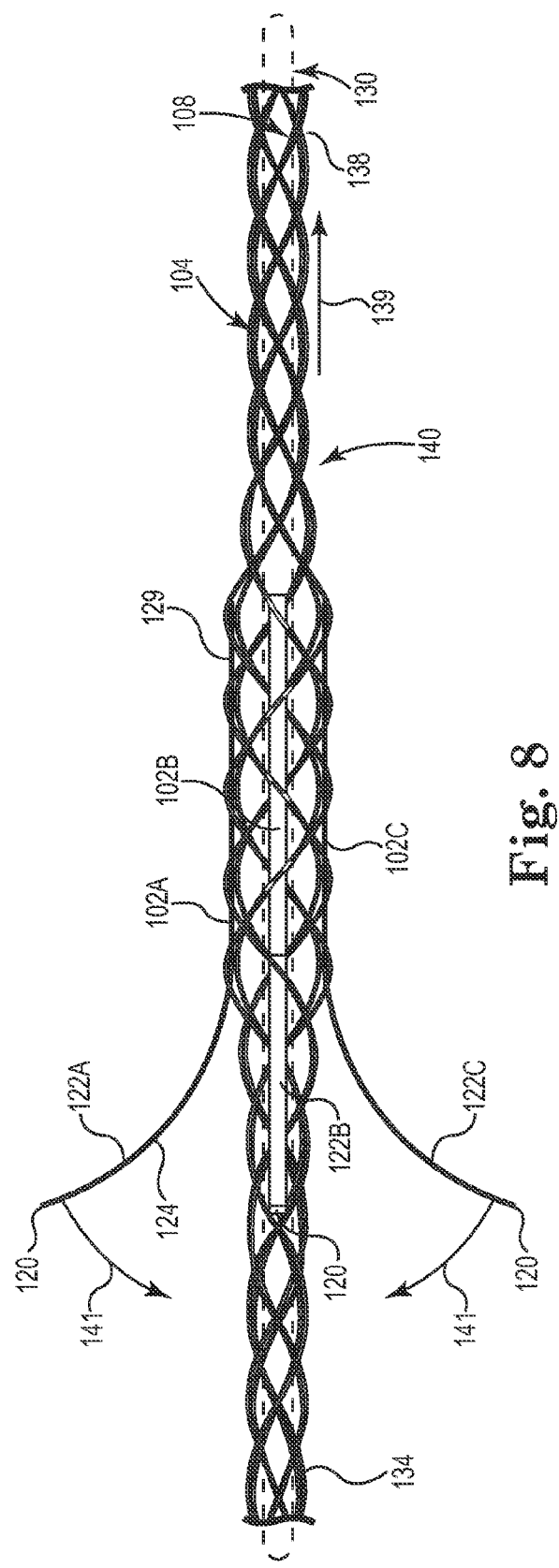

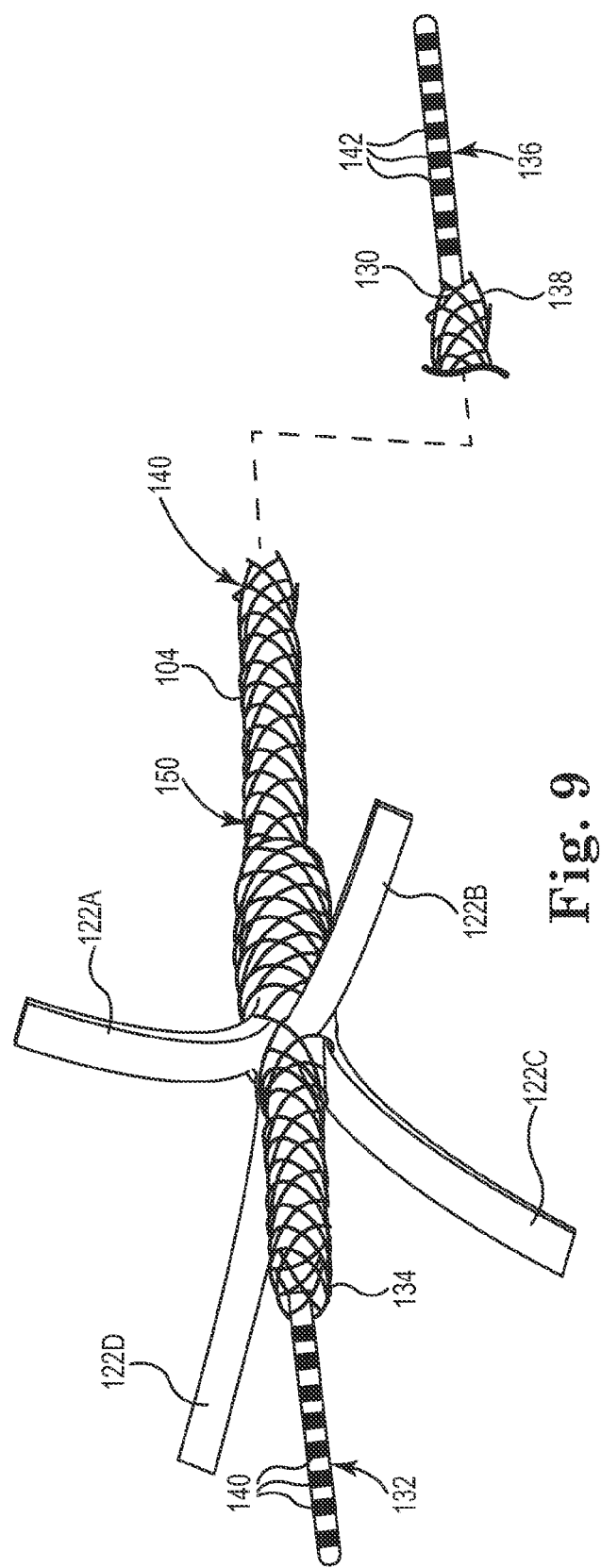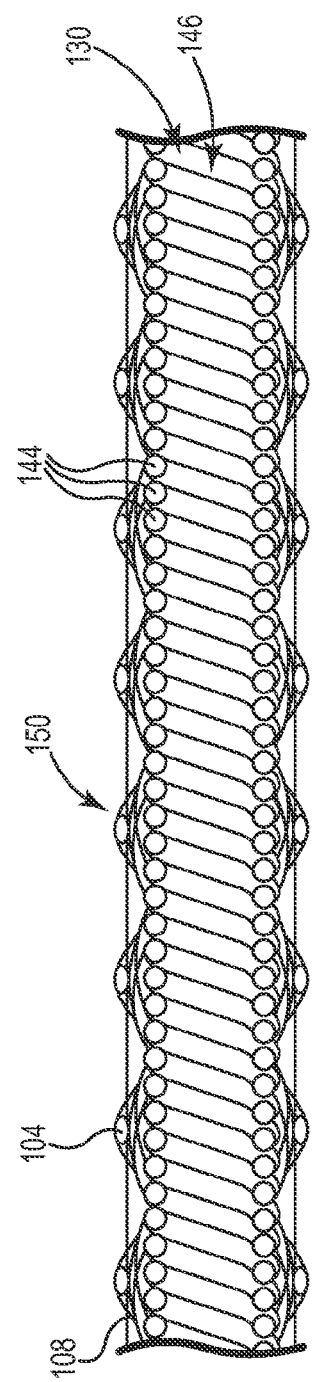

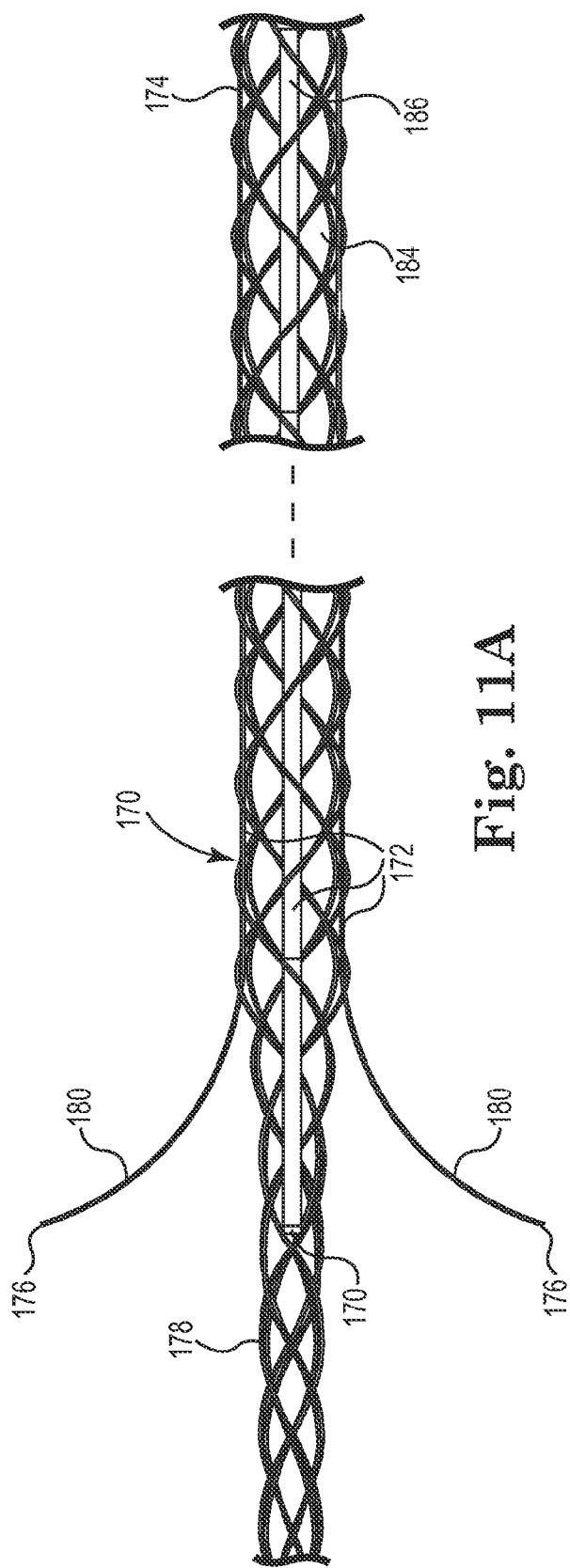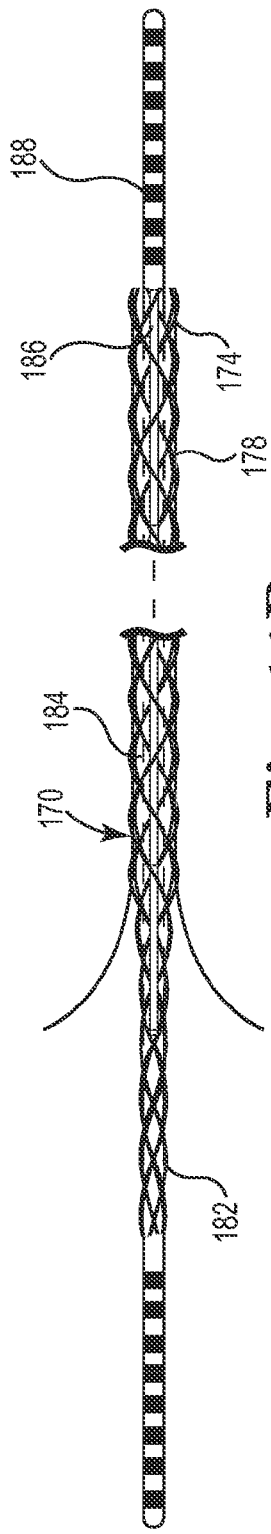

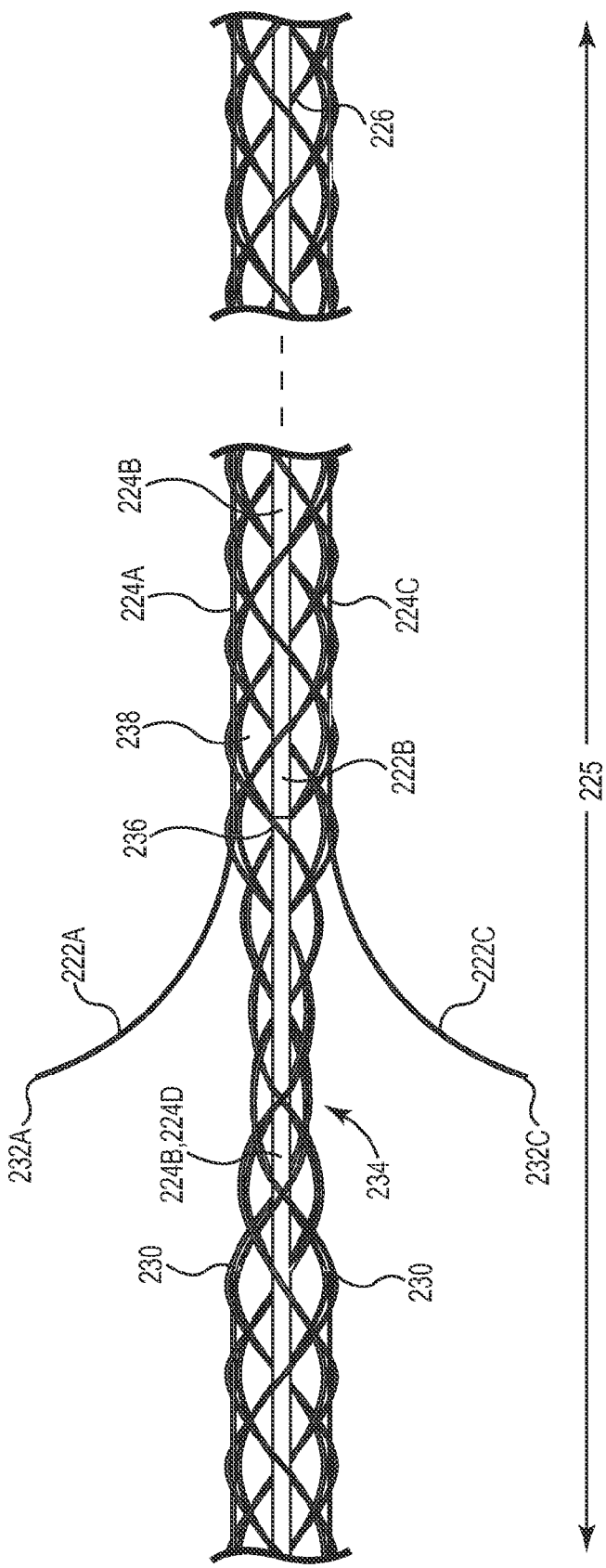
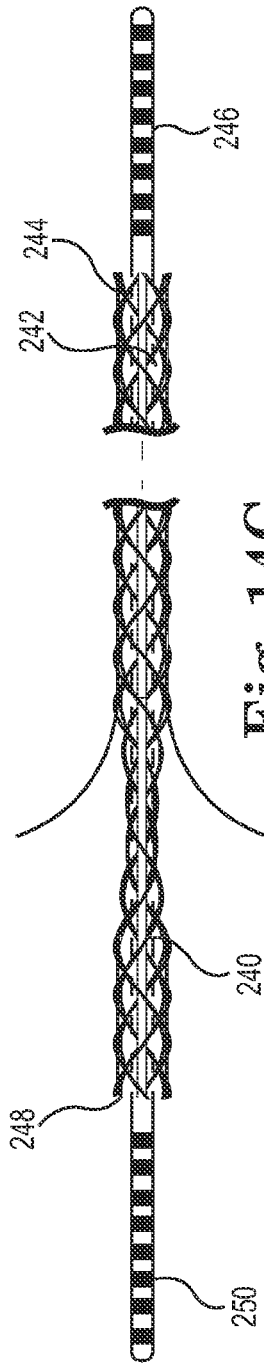
Fig. 14B
Fig. 14C

BRAIDED LEAD WITH EMBEDDED FIXATION STRUCTURES

FIELD

The present disclosure is directed to a method and apparatus that allows for stimulation of body tissue, particularly nerves. More specifically, this disclosure relates to a reinforced implantable medical electrical lead having at least one fixation structure for providing stability for the stimulation electrodes. Moreover, this disclosure relates to the method of implantation and anchoring of the medical electrical lead electrodes in operative relation to a selected nerve to allow for stimulation.

BACKGROUND

Implantable medical electronics devices consist of an implanted pulse generator that is used to provide electrical stimulation to certain tissues and an implantable lead or leads that are used to transmit the electrical impulse to the targeted tissues. Examples include cardiac pacemaking, and a number of related applications for cardiac rhythm management, treatments for congestive heart failure, and implanted defibrillators. Other applications for implantable pulse generators include neurostimulation with a wide range of uses such as pain control, nervous tremor mitigation, incontinent treatment, epilepsy seizure reduction, vagus nerve stimulation for clinical depression, and the like.

Despite various suture fixation devices, nerve stimulation leads can be dislodged from the most efficacious location due to stresses placed on the lead by the ambulatory patient. A surgical intervention is then necessary to reposition the electrode and affix the lead. The implantable pulse generator ("IPG") is programmed to deliver stimulation pulse energy to the electrode providing the optimal nerve response. The efficacy of the selected electrode can fade over time due to dislodgement or other causes.

Physicians spend a great deal of time with the patient under a general anesthetic placing the small size stimulation electrodes relative to the target nerves. The patient is thereby exposed to the additional dangers associated with extended periods of time under a general anesthetic. Movement of the lead, whether over time from suture release or during implantation during suture sleeve installation, is to be avoided. As can be appreciated, unintended movement of any object positioned proximate a nerve may cause unintended nerve damage. Moreover reliable stimulation of a nerve requires consistent nerve response to the electrical stimulation that, in turn, requires consistent presence of the stimulation electrode proximate the target nerve. On the other hand, if the target nerve is too close to the electrode, inflammation or injury to the nerve can result, diminishing efficacy and possibly causing patient discomfort.

Cardiac pacing leads are commonly provided with passive fixation mechanisms that non-invasively engage heart tissue in a heart chamber or cardiac blood vessel or active fixation mechanisms that invasively extend into the myocardium from the endocardium or epicardium. Endocardial pacing leads having pliant tines that provide passive fixation within interstices of trabeculae in the right ventricle and atrial appendage are well known in the art as exemplified by U.S. Pat. Nos. 3,902,501; 3,939,843; 4,033,357; 4,236,529; 4,269,198; 4,301,815; 4,402,328; 4,409,994; and 4,883,070, for example. Such tined leads typically employ tines that extend outwardly and proximally from a band proximal to a distal tip pace/sense electrode and that catch in natural trabecular interstices when the distal tip electrode is advanced into the a trial appendage or the ventricular apex.

Certain spinal cord stimulation leads have been proposed employing tines and/or vanes as stand-offs to urge the stimulation electrode in the epidural space toward the spinal cord as disclosed in U.S. Pat. Nos. 4,590,949 and 4,658,535, for example, and to stabilize the stimulation electrode in the epidural space as disclosed in U.S. Pat. No. 4,414,986, for example.

Stimulation leads for certain pelvic floor disorders have been proposed with a fixation mechanism that includes a plurality of tine elements arrayed in a tine element array along a segment of the lead proximal to the stimulation electrode array, such as for example in U.S. Pat. Nos. 6,999,819; 7,330,764; 7,912,555; 8,000,805; and 8,036,756. Each tine element includes a plurality of flexible, pliant, tines. The tines are configured to be folded inward against the lead body when fitted into and constrained by the lumen of an introducer.

Peripheral nerve field stimulation ("PNFS") involves delivery of stimulation to a specific peripheral nerve via one or more electrodes implanted proximate to or in contact with a peripheral nerve, such as disclosed in U.S. Pat. Publication No. 2009/0281594. PNFS may be used to deliver stimulation to, for example, the vagal nerves, cranial nerves, trigeminal nerves, ulnar nerves, median nerves, radial nerves, tibial nerves, and the common peroneal nerves. When PNFS is delivered to treat pain, one or more electrodes are implanted proximate to or in contact with a specific peripheral nerve that is responsible for the pain sensation.

Tined leads can create problems during removal or explant. In particular, the human body recognizes a lead as a foreign body and forms fibrous tissue around the lead. The fibrous tissue strengthens the engagement with the tines. If the anchoring of the tines is stronger than the lead itself, the lead may break during removal, leaving fragments behind. These fragments can migrate creating pain and increasing the risk of infection. Additional surgery is often required to remove the fragments.

BRIEF SUMMARY

The present disclosure is directed to a therapy delivery element configured for at least partial insertion in a living body. The therapy delivery element includes a plurality of fibers braided to form an elongated braided structure with a lumen. At least one reinforcing structure is woven into the fibers of the braided structure. A portion of the reinforcing structure extends from the braided structure to form a fixation structure. A conductor assembly including a plurality of conductors is located in the lumen. An electrode assembly is located at a distal end of the conductor assembly. The electrode assembly includes a plurality of electrodes that are electrically coupled to the conductors. A connector assembly is located at a proximal end of the conductor assembly. The connector assembly includes a plurality of electrical contacts that are electrically coupled to the conductors. At least one of the braided structure or the reinforcing structure is attached to at least one of the electrode assembly or the connector assembly.

The braided structure can be attached to both the electrode assembly and the connector assembly. The reinforcing structure is preferably attached to at least the connector assembly. At least one reinforcing structure preferably extends substantially the entire length of the braided structure.

In one embodiment, a tubular structure surrounds the braided structure. The tubular structure is preferably bonded to the braided structure. In one embodiment, the tubular structure is a thermoplastic material melted into engagement with the braided structure. The at least one reinforcing structure is preferably bonded to the braided structure.

The fixation structure is preferably a distal end of the at least one reinforcing structure pulled from the braided structure. The fixation structures can be distal ends of a plurality of the reinforcing structures pulled from the braided structure to form a plurality of fixation structures. The braided structure preferably includes least one reinforcing structure that extends the entire length of the braided structure. The fixation structures preferably have a shape configured to fold against the lead body during removal of the therapy delivery element from the living body.

In one embodiment, a plurality of fixation structures is radially spaced around the elongated braided structure. The fixation structures can be axially and/or radially offset along the elongated braided structure.

The braided structure and the reinforcing structure increase the tensile strength of the therapy delivery element by about at least about 15%, and more preferably at least about 30%. The fixation structures preferably have a length of at least about 0.050 inches.

The present disclosure is also directed to a neurostimulation system including an implantable pulse generator. A therapy delivery element as discussed herein is provided. The electrical contacts on the connector assembly are configured to electrically couple with the implantable pulse generator. At least one of the braided structure or the reinforcing structure is attached to at least one of the electrode assembly or the connector assembly.

The present disclosure is also directed to a method of making a therapy delivery element configured for at least partial insertion in a living body. The method includes braiding a plurality of fibers to form an elongated braided structure with a lumen. At least one reinforcing structure is woven into the fibers of the braided structure. A portion of the reinforcing structure extends from the braided structure to form at least one fixation structure. A conductor assembly with a plurality of conductors is located in the lumen of the braided structure. Electrodes on an electrode assembly are electrically coupled to the conductors. The electrode assembly is attached to a distal end of the conductor assembly. Electrical contacts on a connector assembly are electrically coupled to the conductors. The connector assembly is attached to a proximal end of the conductor assembly. At least one of the braided structure or the reinforcing structure is attached to at least one of the electrode assembly and the connector assembly.

The method optionally includes attaching both the electrode assembly and the connector assembly to the braided structure. The method also optionally includes attaching the reinforcing structure to at least the connector assembly. In one embodiment, the method includes locating a tubular structure around the braided structure and bonding the tubular structure to the braided structure.

In one embodiment, a distal end of at least one reinforcing structure is removed from the braided structure to form the fixation structure. The fixation structure can be shaped to fold against the lead body during removal of the therapy delivery element from the living body.

BRIEF DESCRIPTION OF THE DRAWINGS

FIG. 7 is a side view of a lead body with reinforcing structures in accordance with an embodiment of the present disclosures.

FIG. 8 is a side view of a lead body with fixation structures in accordance with an embodiment of the present disclosure.

FIG. 9 is a perspective view of a therapy delivery element with fixation structures in accordance with an embodiment of the present disclosure.

FIG. 10 is a side sectional view of a conductor assembly in the lead body of FIG. 9 in accordance with an embodiment of the present disclosure.

FIG. 11A is a side view of a lead body with fixation structures in accordance with an embodiment of the present disclosures.

FIG. 11B is a side view of a therapy delivery element including the lead body of FIG. 11A in accordance with an embodiment of the present disclosure.

FIG. 14B is a side view of the lead body of FIG. 14A.

FIG. 14C is a side view of a therapy delivery element including the lead body of FIG. 14B in accordance with an embodiment of the present disclosure.

The drawings are not necessarily to scale. Like numbers refer to like parts or steps throughout the drawings.

DETAILED DESCRIPTION OF SOME EMBODIMENTS

The description that follows highlights spinal cord stimulation (SCS) system, the treatment of pelvic floor disorders, and peripheral nerve field stimulation (PNFS). However, it is to be understood that the disclosure relates to any type of implantable therapy delivery system with one or more therapy delivery elements with one or more electrodes or sensors. For example, the present disclosure may be used as part of a pacemaker, a defibrillator, a cochlear stimulator, a retinal stimulator, a stimulator configured to produce coordinated limb movement, a cortical stimulator, a deep brain stimulator, microstimulator, or in any other neural stimulator configured to treat sleep apnea, shoulder sublaxation, headache, etc.

In another embodiment, one or more of the therapy delivery elements may be a fluid or drug delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be a medical electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
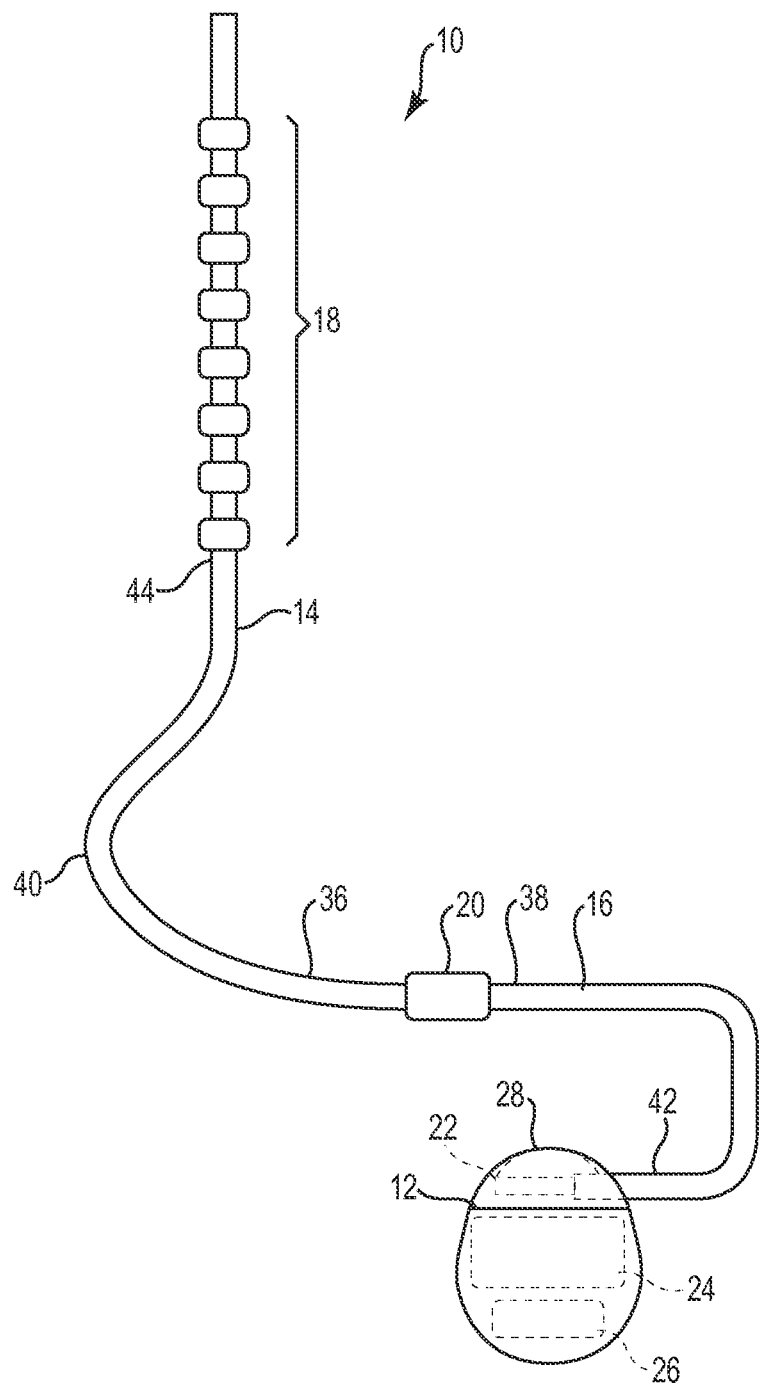
FIG. 1 is a schematic illustration of a therapy delivery system.

FIG. 1 illustrates a generalized therapy delivery system 10 that may be used in stimulation applications. The therapy delivery system 10 generally includes an implantable pulse generator 12 ("IPG") ("IPG"), an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes lead body 40 having a proximal end 36 and a distal end 44. The lead body 40 typically has a diameter ranging between about 0.03 inches to about 0.07 inches and a length ranging between about 30 cm to about 90 cm for spinal cord stimulation applications. The lead body 40 may include a suitable electrically insulative coating, such as, a polymeric material (e.g., polyurethane or silicone).

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2A:
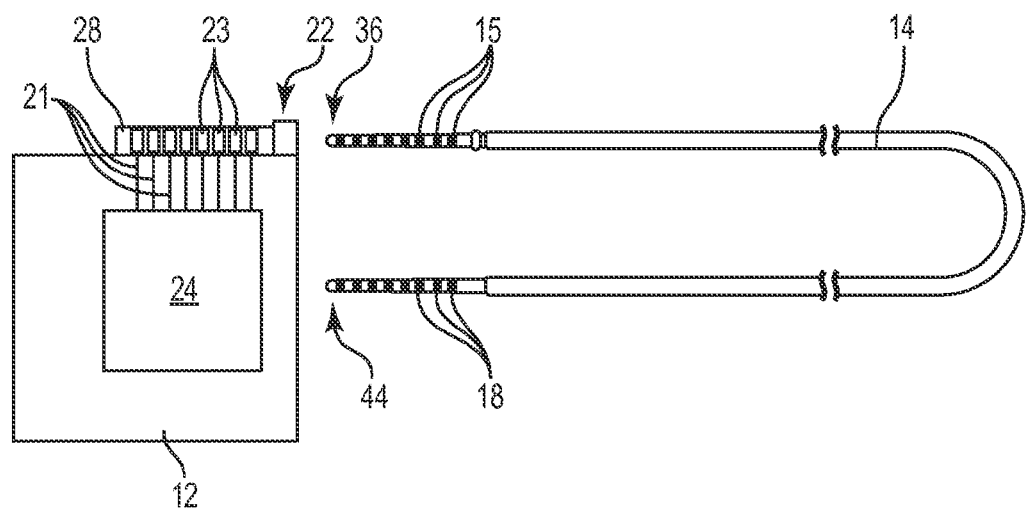
FIG. 2A is a schematic illustration of an implantable pulse generator and a therapy delivery element in accordance with an embodiment of the present disclosure.

FIG. 2A illustrates the therapy delivery element 14 including one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22. In the embodiment illustrated in FIGS. 2A and 2B, the therapy delivery element 14 forms a medical electrical lead.

The connector assembly 22 includes a plurality of discrete contacts 23 located in the housing 28 that electrically couple contact rings 15 on the proximal end of the therapy delivery element 14. The discrete contacts 23 are electrically coupled to circuitry 24 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can be configured to independently deliver electrical impulses to each of the electrodes 18.

Figure 2B:
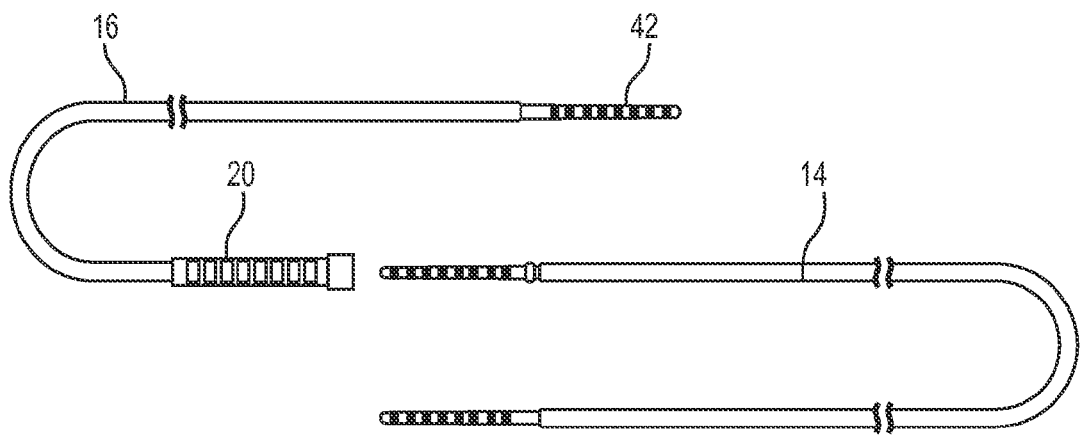
FIG. 2B is a schematic illustration of a lead extension and a therapy delivery element in accordance with an embodiment of the present disclosure.

Alternatively, the therapy delivery element 14 can be coupled to the implantable pulse generator 12 through one or more lead extensions 16, as illustrated in FIG. 2B. The connector 20 at the distal end 38 of the lead extension 16 preferably includes a plurality of the contacts 23 configured in a manner similar to the connector assembly 22.

Figure 3:
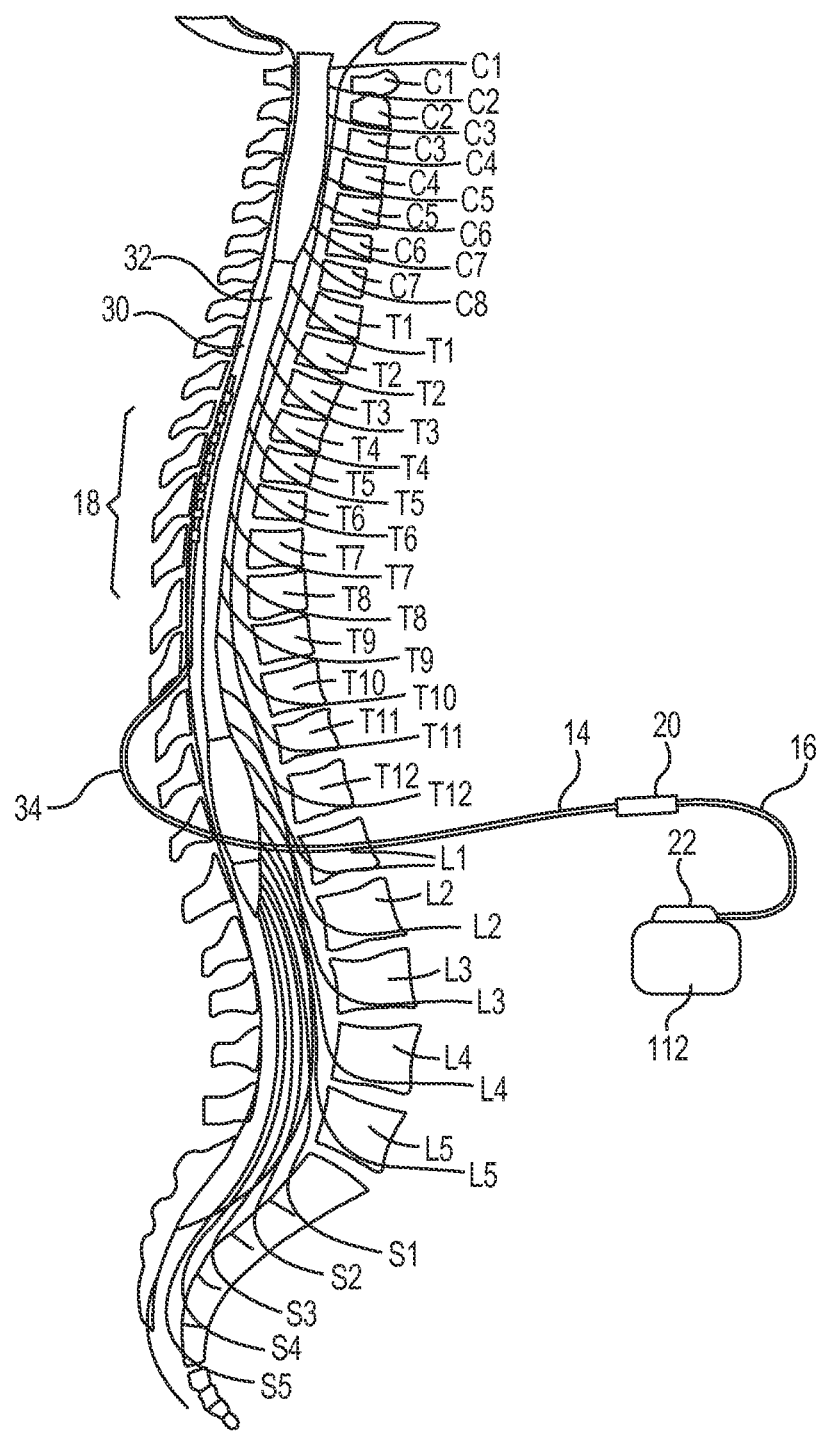
FIG. 3 is a schematic illustration of a therapy delivery system for spinal cord stimulation in accordance with an embodiment of the present disclosure.

FIG. 3 illustrates the therapy delivery element 14 used for spinal cord stimulation (SCS) implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as the proximate sacral nerves.

Figure 4:
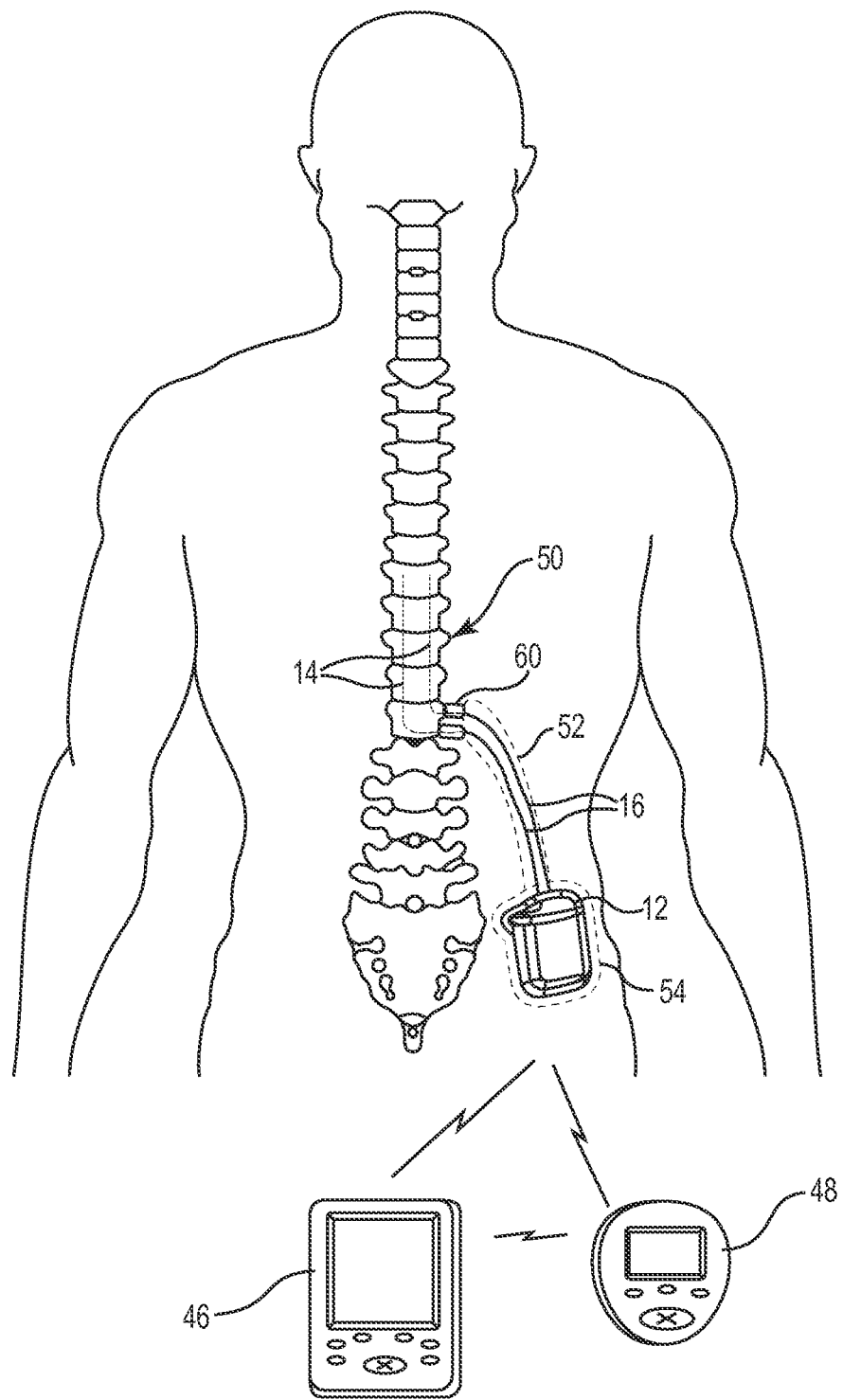
FIG. 4 is an alternate illustration of an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 4. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 4, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" may be used interchangeably, unless context indicates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 5:
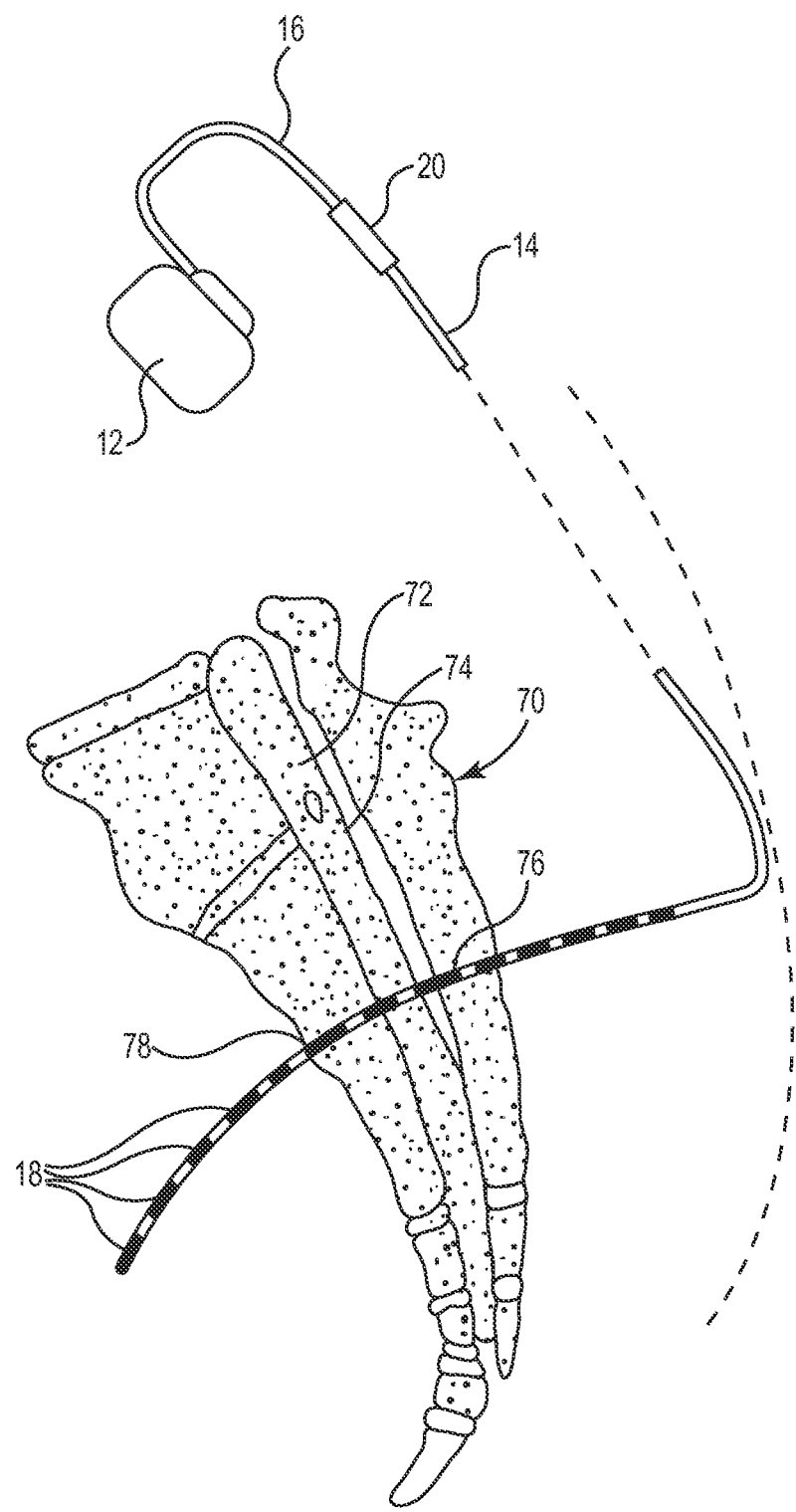
FIG. 5 is a schematic illustration of a therapy delivery system for treating pelvic floor disorders in accordance with an embodiment of the present disclosure.

FIG. 5 illustrates the therapy delivery element 14 used for pelvic floor disorders such as, urinary incontinence, urinary urge/frequency, urinary retention, pelvic pain, bowel dysfunction (constipation, diarrhea), erectile dysfunction, are bodily functions influenced by the sacral nerves. The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles 72 within the sacrum 70. The sacrum 70, generally speaking, is a large, triangular bone situated at the lower part of the vertebral column, and at the upper and back part of the pelvic cavity. The spinal canal 74 runs throughout the greater part of the sacrum 70. The sacrum is perforated by the posterior sacral foramina 76 and anterior sacral foramina 78 that the sacral nerves 70 pass through.

Specifically, urinary incontinence is the involuntary control over the bladder that is exhibited in various patients. The therapy delivery element 14 is percutaneously implanted through the foramina 76, 78 of the sacral segment S3 for purposes of selectively stimulating the S3 sacral nerve 72. Stimulation energy is applied through the lead 14 to the electrodes 18 to test the nerve response. The electrodes 18 are moved back and forth to locate the most efficacious location, and the lead 14 is then secured by suturing the lead body to subcutaneous tissue posterior to the sacrum 70 and attached to the output of a neurostimulator IPG 12.

Figure 6:
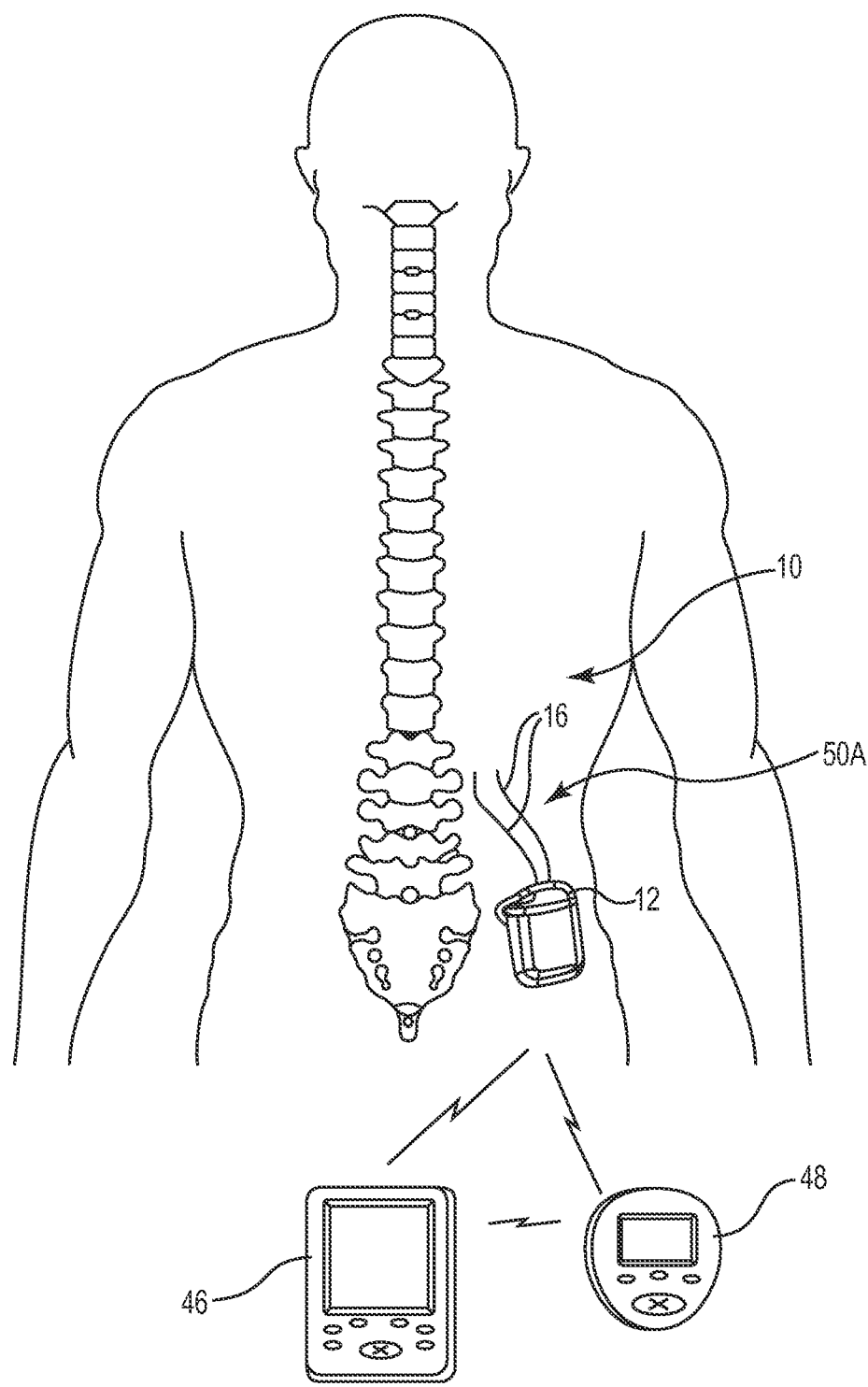
FIG. 6 is a schematic illustration of a therapy delivery system for peripheral nerve stimulation in accordance with an embodiment of the present disclosure.

FIG. 6 illustrates the therapy delivery element 14 used for delivering peripheral nerve field stimulation (PNFS) to a patient. Therapy delivery element 14 delivers PNFS from the implantable pulse generator 12 to the tissue of patient at target location 50A where patient experiences pain. Clinician programmer 46 and patient programmer 48 may communicate via wireless communication with the implantable pulse generator 12.

Therapy delivery element 14 may be implanted within or between, for example, intra-dermal, deep dermal, or subcutaneous tissue of patient at the location 50A where patient experiences pain. Subcutaneous tissue includes skin and associated nerves, and muscles and associated nerves or muscle fibers. In the illustrated example, location 50A is a region of the lower back. In other examples, the therapy delivery element 14 may extend from implantable pulse generator 12 to any localized area or dermatome in which patient experiences pain, such as various regions of the back, the back of the head, above the eyebrow, and either over the eye or under the eye, and may be used to treat failed back surgery syndrome (FBBS), cervical pain (e.g., shoulder and neck pain), facial pain, headaches supra-orbital pain, inguinal and pelvic pain, chest and intercostal pain, mixed pain (e.g., nociceptive and neuropathic), visceral pain, neuralgia, peroneal pain, phantom limb pain, and arthritis.

FIG. 7 is a side view of a lead body 100 including a plurality of reinforcing members 102 embedded in braided structure 104 in accordance with an embodiment of the present disclosure. The braided structure 104 includes a plurality of fibers 106 that are braided around the reinforcing member 102. The fibers 106 capture the reinforcing member 102 within the braided structure 104. Lumen 108 extending the full length 112 of the lead body 100 and is sized to receive a conductor assembly (see e.g., FIG. 8).

The braided structure 104 is preferably an axial braid, although a variety of other braid patterns or woven structures may be used. As used herein, "braid" or "braided" refers to structures formed by intertwining or weaving three or more strands or fibers of a flexible material. Braids are preferred because of high tensile strength and good radial flexibility. The braided structure 104 reinforces the lead body during ex-plant without losing flexibility. Another advantage of the braided structure 104 is that braids neck down when a tensile load is applied. The reduced cross-sectional diameter of the braided structure 104 during ex-plant facilitates removal and acts to pull the fixation structures 122 (see FIG. 8) inward to promote disengagement from the surrounding tissue.

The fibers 106 are preferably a bio-compatible polymeric material, such as for example, polyethylene terephthalate (PET), Nylon, polyether ether ketone (PEEK), polyproylene, high-performance polyethylenes, bioabsorbale polymers, such as polyglutamic acid (PGA), poly-L-lactide (PLLA), or polycaprolactone (PCL), urethane, silicone, Nitinol, stainless steel, MP35N, titanium, or any combination of these materials. Any number of discrete fibers 106 can be used in the braid structure 104, but typically there are about 4 to about 16 fibers. In one embodiment, some portion of the fibers 106 run clockwise and the remainder run counterclockwise within the braided structure 104.

The fibers 106 are preferably a mono-filament with a diameter in a range of about 0.001 inches to about 0.006 inches. Selection of the fibers 106 depends on a variety of variables, such as for example, diameter 110 of the lead body, overall length 112, and the intended application. In one embodiment, the braided structure 104 includes about 12 fibers 106 made from PET, each having a diameter of about 0.004 inches. The lumen 108 preferably has a diameter ranging between about 0.01 inches to about 0.035 inches.

In another embodiment, some of the fibers 106 are made from a conductive material, like copper, platinum, MP35N, or silver, to provide shielding and grounding for the resulting therapy delivery element. For example, some of the fibers 106 are optionally made from a conductive material to provide shielding to the lead.

The reinforcing members 102 are preferably a plurality of discrete structures captured within the braided structure 104. The reinforcing members 102 can have a variety of cross-sectional shapes, such as for example, circular, oval, rectangular, and the like. In the illustrated embodiment, the reinforcing member has a cross-sectional shape with width 114 in a range between about 0.01 inches to about 0.04 inches and thickness 116 in a range between about 0.005 inches to about 0.020 inches.

The reinforcing members 102 can be constructed from a variety of bio-compatible materials, such as metals, polymeric materials, and composites thereof, such as for example, PET, nylon, PEEK, polyproylene, high-performance polyethylenes, bioabsorbable polymers such as PGA, PLLA, or PCL, urethanes such as Tecothane®, silicone, Nitinol, stainless steel, MP35N, titanium, or combination thereof. Tecothane® aromatic polyether-based thermoplastic polyurethanes are resins which exhibit solvent resistance and biostability over a wide range of hardness. The reinforcing members 102 are optionally constructed from a radiopaque filled material.

The reinforcing members 102 in a single lead body can be the same material and shape. Alternatively, the reinforcing members 102 can have different cross sectional shapes and/or different materials in order to promote preferential bending.

The number of reinforcing members 102 in the lead body 100 can vary from one to as many as can physically fit within the braided structure 104. The reinforcing structure 102 can be located in specific axial locations of the braided structure 104, or run the entire length 112 of the braided structure 104. The reinforcing members 102 are preferably axially oriented, generally parallel to central axis of the lead body 100.

The reinforcing members 102 may be secured to the braided structure 104 simply by friction with the fibers 106. In another embodiment, the reinforcing members 102 can be bonded to the braided structure 104 using a variety of techniques. As used herein "bonded" or "bonding" refers to adhesive bonding, solvent bonding, ultrasonic welding, thermal bonding, and a variety of other techniques.

The braided structure 104 plus the reinforcing members 102 increase the tensile strength of the lead body 100 by about at least about 15%, and more preferably at least about 30% relative to comparable leads without the braided structure 104 or reinforcing members 102. In embodiments where the braided structure 104 includes metal wires and/or the reinforcing members 102 are metal, the tensile strength of the lead body 100 increases at least about 30% to about 60%.

FIGS. 8 and 9 illustrate an example including four the reinforcing member 102A, 102B, 102C, 102D ("102") are oriented generally parallel within the lumen 108. In order to minimize the diameter 110 of the lead body 100 the reinforcing members 102 preferably do not overlap.

Distal ends 120 of the reinforcing members 102 are pulled free from the braided structure 104 to form fixation structures 122A, 122B, 122C, 122D ("122"). The exposed portion of the reinforcing member 102 can be shaped as desired to enhance the securing properties of the fixation structures 122. For example, the fixation structures 122 can be heat-set to create a desired shape, such as curvature 124.

The shape of the fixation structures 122 facilitates removal of the therapy delivery element 140 from the patient. During removal the surgeon grasps proximal end 138 and applies a force 139 in the direction indicated. As the therapy delivery element 140 is displaced in direction 139 the fixation structures 122 tend to fold in direction 141 toward the lead body 100. The braided structure 104 tends to neck down in response to the force 139, which reduces cross-sectional diameter of the braided structure 104 to facilitate removal. The necking down also promotes disengagement of the fixation structures 122 from the surrounding tissue.

In one embodiment, the reinforcing members 102 have a length 128 less than, or equal to, the length 112 of the lead body 100. Portions 129 of the reinforcing members 102 retained in the braided structure 104 have a length of at least one inch. The length of the portions 129 may vary depending upon whether the reinforcing members 102 are bonded to the braided structure 104. Consequently, the fixation structures 122 typically have a length in a range between about 0.050 inches to about 0.300 inches.

Conductor assembly 130 is located in the lumen 108 of the lead body 100 to form therapy delivery element 140. The conductor assembly 130 includes one or more conductors 144 (see e.g., FIG. 10) extending through the lumen 108 from electrode assembly 132 located at distal end 134 to connector assembly 136 located at proximal end 138. Typically there is a one-to-one correlation between the number of electrodes 140, connectors 142 and conductors 144. For example, if there are eight electrodes 140 and eight connectors 142, the conductor assembly 130 includes eight conductors 144. As used herein, "conductor assembly" refers to one or more insulated or un-insulated conductive wires or cables arranged in a variety of configurations, including straight, coiled, braided, and the like, that electrically couple electrodes at one end of a lead body to connectors at an opposite end.

The braided structure 104 preferably extends onto and is bonded to the electrode assembly 132 and the connector assembly 134. In this embodiment, the braided structure 104 works in conjunction with the conductor assembly 130 to increase the tensile strength of the resulting therapy delivery element.

FIG. 10 is a cross-sectional view of the lead body 100 in region 150 where the reinforcing members 102 are not present. The illustrated segment of the conductor assembly 130 includes a plurality of discrete conductors 144 arranged in coil form to create lumen 146 generally concentric with lumen 108 formed by the braided structure 104. Alternate coil configurations are disclosed in commonly assigned U.S. application Ser. No. 13/045,908, entitled Implantable Lead with Braided Conductors, filed Mar. 11, 2011; U.S. application Ser. No. 13/220,913, entitled Lead Body with Inner and Outer Co-Axial Coils, filed Aug. 30, 2011, which is hereby incorporated by reference.

The lumen 146 can optionally be used to receive a stylet that increases the rigidity and column strength of the therapy delivery element 140 during implantation. Suitable stylets are disclosed in commonly assigned U.S. patent application Ser. No. 13/222,018, entitled Adjustable Wire Length Stylet Handle, filed Aug. 31, 2011, and in U.S. Pat. Nos. 6,214,016; 6,168,571; 5,238,004; 6,270,496 and 5,957,966, all of which are hereby incorporated by reference.

The conductors 144 can in include single conductive element, a plurality of conductive wires, or a combination thereof. For example, each conductor 144 optionally includes a plurality of un-insulated conductive wires twisted in a rope-like configuration or cable. Each individual cable is insulated. The individual wires can be homogenous or a multi-layered structure. For example, the core can be silver or copper and the outer layer can be a nickel-cobalt-chromium-molybdenum alloy, such as for example, MP35N. According to one embodiment, the cable included seven 0.005 inch diameter, silver core MP35N conductors arranged in a 1×7 configuration and covered with an ETFE (ethylene tetrafluoroethylene) coating.

FIG. 11A illustrates an alternate lead body 170 in which reinforcing members 172 extend substantially to proximal end 174 in accordance with an embodiment of the present disclosure. Distal ends 176 of the reinforcing members 172 are pulled free from the braided structure 178 to form fixation structures 180, as discussed herein.

As illustrated in FIG. 11B, conductor assembly 182 is then located in lumen 184 of the lead body 170. Proximal ends 186 of the reinforcing structures 172 preferably extend substantially to the connector assembly 188. In one embodiment, both the braided structure 178 and the proximal ends 186 of the reinforcing structures 172 are attached to the connector assembly 188.

Figure 12:
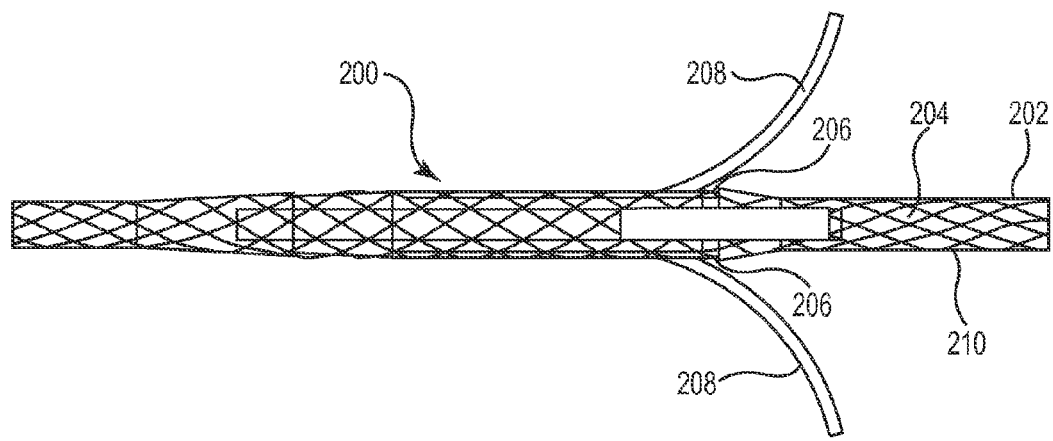
FIG. 12 is a side view of an alternate lead body with integral fixation structures in accordance with an embodiment of the present disclosure.

FIG. 12 is a side view of an alternate lead body 200 with an outer tube 202 located over the braided structure 204 in accordance with an embodiment of the present disclosure. Rectangular channels 206 are cut in the outer tube 202 to permit reinforcing members 208 to extend outward from the lead body 200. The outer tube 202 serves to increase the tensile strength of the lead body 200 and to seal the braided structure 204 so the lead body is suitable for permanent implantation. Without the outer tube 202 there is a risk that tissue will grow around the braided structure 204, making removal from the patient difficult. In one embodiment, the outer tube 202 is fused or bonded to the braided structure 204, such as for example, by reflowing the outer tube 202.

In addition to preventing tissue in-growth, the added body tubing also helps to increase the tensile strength of the lead. Lab testing on lead samples with various braided polymers (materials ranging from plastics to metal) and reflowed body tubing showed a yield strength in a range between about 15% to about 60% greater than tradition 4 conductor leads without the present reinforcing structure.

Figure 13:
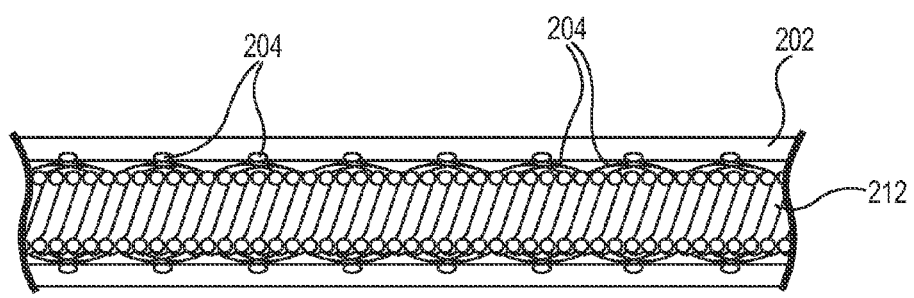
FIG. 13 is a side sectional view of a conductor assembly located in the lead body of FIG. 12 in accordance with an embodiment of the present disclosure.

FIG. 13 is a sectional view of segment 210 of the lead body 200 after conductor assembly 212 is installed. The braided structure 204 is embedded in the outer tube 202 due to reflow. While the lead body 100 of FIG. 9 is preferably used for temporary or trial therapy delivery elements, the lead body 200 is suitable for permanent implantation.

Figure 14A:
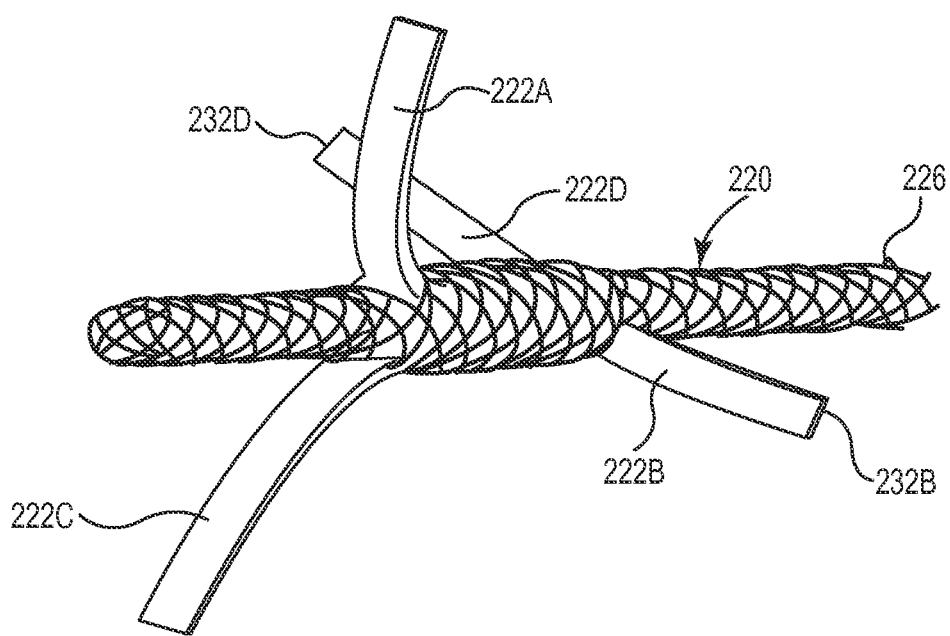
FIG. 14A is a perspective view of a lead body with radially and axially off-set fixation structures in accordance with an embodiment of the present disclosure.

FIG. 14A is a side view of an alternate lead body 220 with axially offset fixation structures 222A, 222B, 222C, 222D ("222") in accordance with an embodiment of the present disclosure. Four reinforcing members 224A, 224B, 224C, 224D ("224") extend substantially the full length 225 of the braided structure 226 and are arranged radially around the braided structure 228 at about 90 degree intervals.

In the illustrated embodiment, fixation structures 222A and 222C are positioned at 0 degrees and 180 degrees radially around the braided structure 226. The fixation structures 222B and 222D are positioned at 90 degrees and 270 degrees, and axially offset from the fixation structures 222B, 222D.

As best illustrated in FIG. 14B, the reinforcing structures 224A and 224C are cut at locations 230 and distal ends 232A, 232C are pulled from the braided structures 226. The braided structure 226 necks-down in gap 234 where the reinforcing structures 224A, 224C are removed. The reinforcing structures 224B, 224D still span the gap 234, however, in order to reinforce the braided structures 226.

Similarly, the reinforcing structures 224B and 224D are cut at locations 236 and distal ends 232B, 232D (see FIG. 14A) are pulled from the braided structures 226. The braided structure 226 necks-down in gap 238 where the reinforcing structures 224B, 224D are removed. The reinforcing structures 224A, 224C span the gap 238 in order to reinforce the braided structures 226. By axially offsetting the reinforcing structures 222A, 222C from the reinforcing structures 222B, 222D, at least two reinforcing structures 224 are available to strengthen the braided structure 226 along the entire length 225. In embodiments where the reinforcing structures 222 are bonded to the braided structure 226, the tensile strength of the lead body 220 is effectively increase by at least the tensile strength of two reinforcing structures 222.

As illustrated in FIG. 11C, conductor assembly 240 is then located in lumen 242 of the lead body 220. Proximal ends 244 of the reinforcing structures 224 and the braided structure 226 are attached to connector assembly 246. Similarly, distal ends 248 of the reinforcing structures 224 and the braided structure 226 are attached to electrode assembly 250.

Figure 15:
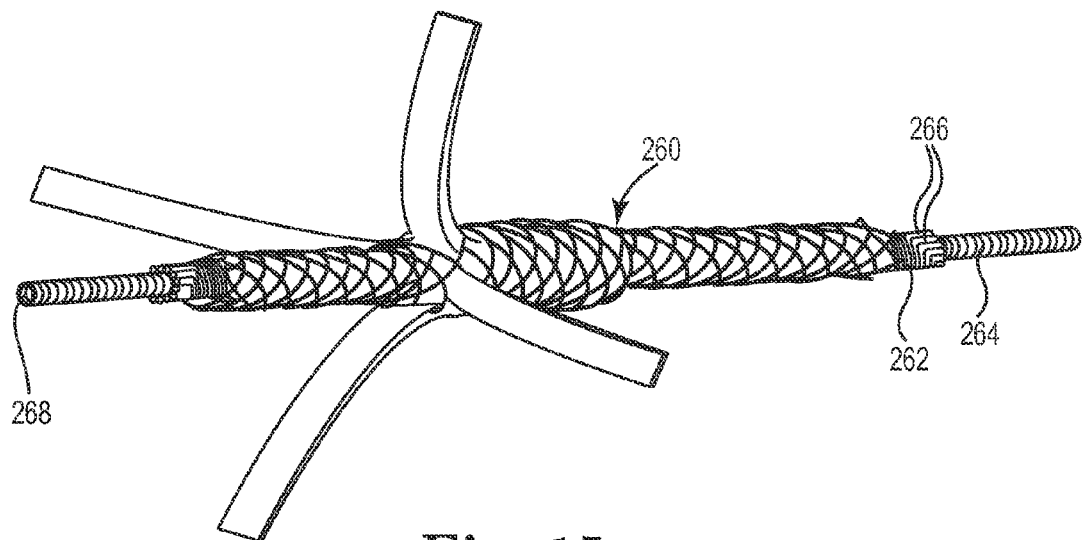
FIG. 15 is an alternate lead body with a conductor assembly having a stylet coil in accordance with an embodiment of the present disclosure.

FIG. 15 illustrates lead body 260 containing conductor assembly 262 including stylet coil 264 in accordance with an embodiment of the present disclosure. The lead body 260 is generally as illustrated in FIG. 9. Conductors 266 are wound around the stylet coil 264. The stylet coil 264 includes lumen 268 sized to receive a stylet wire (not shown).

Figure 16:
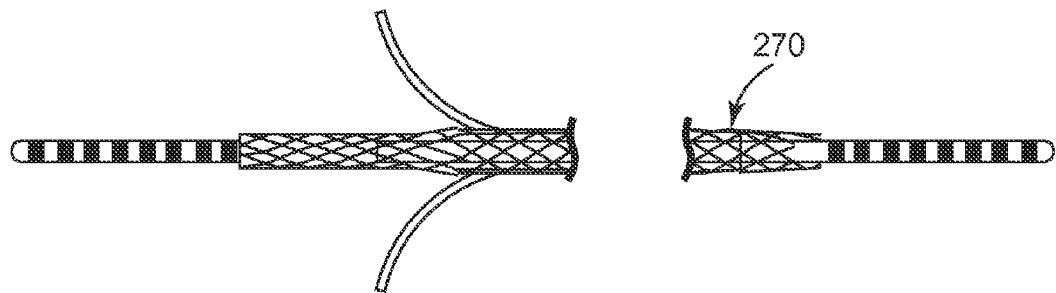
FIG. 16 is a therapy delivery element using the lead body of FIG. 15.

The stylet coil 264 can be a braided structure, a tubular structure, an elongated material formed as a helical coil, or a variety of other structures. In the illustrated embodiment, the stylet coil 264 is a flattened wire configured as a helical coil. The stylet coil 264 protects the conductors 266 from damage from the stylet (not shown) and adds tensile strength to the therapy delivery element 270 (see FIG. 16).

Figure 17:
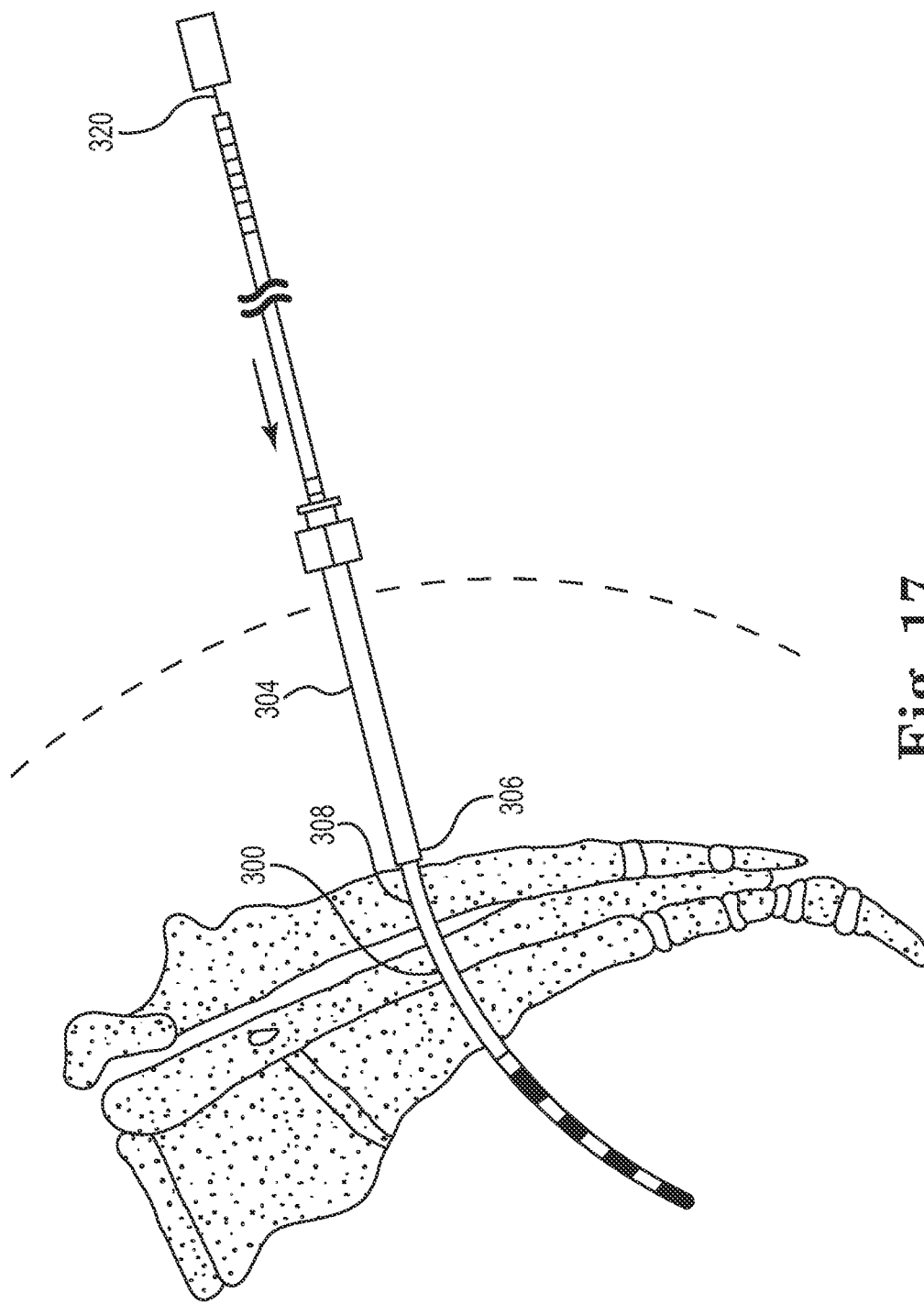
FIG. 17 illustrates a portion of method of implanting a therapy delivery element in accordance with an embodiment of the present disclosure.

FIG. 17 illustrates one embodiment of a therapy delivery element 300 in sacral nerve in accordance with an embodiment of the present disclosure. The therapy delivery element 300 and the fixation structures 302 (see FIG. 18) are disposed within introducer 304. The introducer 304 is advanced percutaneously at a selected angle until the introducer distal end 306 is disposed at the selected foramen 308. The therapy delivery element 300 may be inserted near any of the sacral nerves including the S1, S2, S3, or S4, sacral nerves accessed via the corresponding foramen depending on the necessary or desired physiologic response.

In one embodiment, the advancement of the introducer 304 can be accomplished separately over a guide wire previously percutaneously advanced from the skin incision into the foramen to establish the angle of advancement. In yet another embodiment, a multi-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately result in the introducer 304 at the location of FIG. 18. The therapy delivery element 300 is optionally stiffened by stylet 320 disposed in the lumen.

Figure 18:
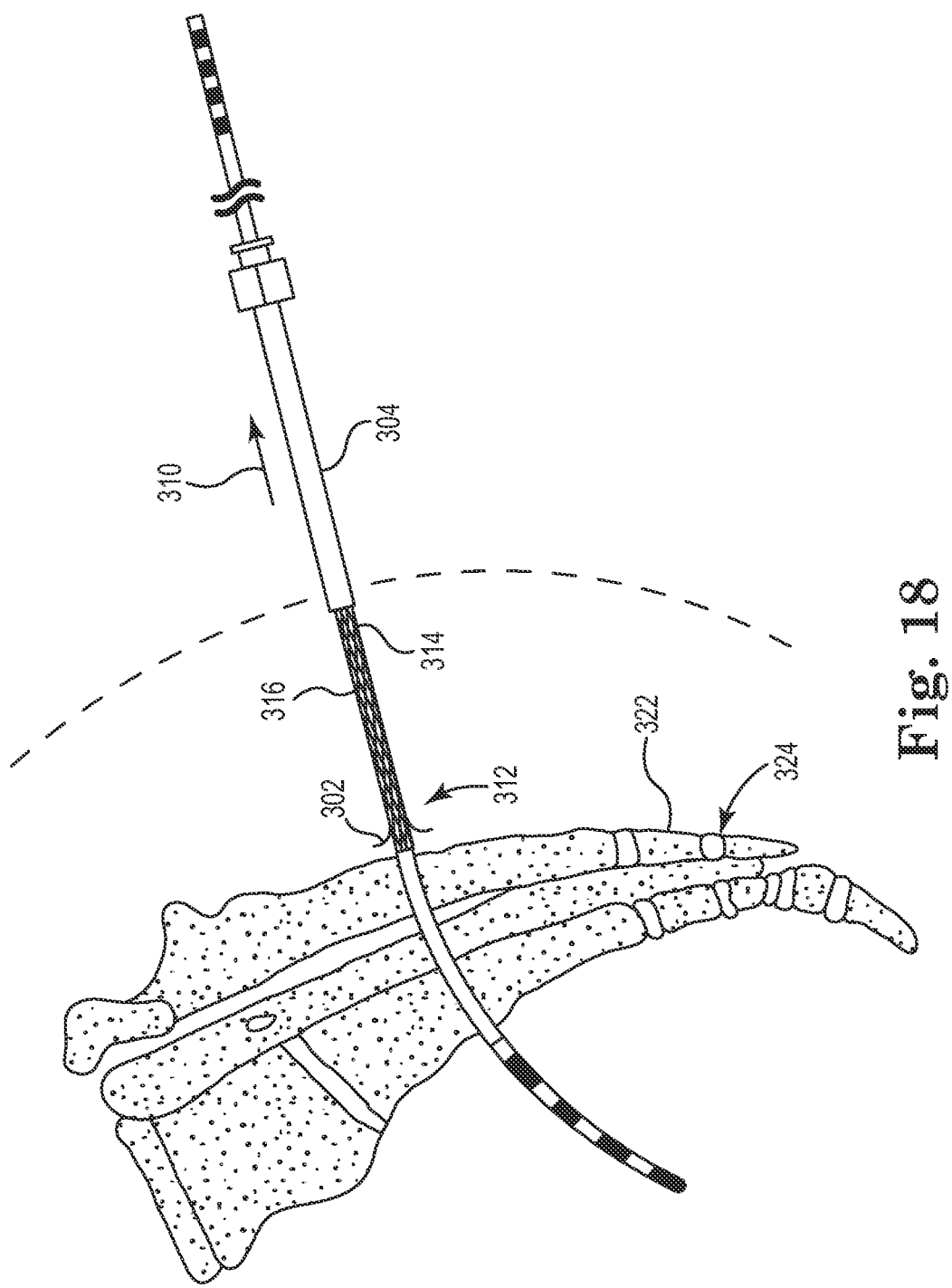
FIG. 18 illustrates a portion of a method of implanting a therapy delivery element in accordance with an embodiment of the present disclosure.

As illustrated in FIG. 18, the introducer 304 is retracted proximally in direction 310 after electrical testing of the therapy delivery element 300. The fixation structures 302 are released from the introducer 304 and engage with surrounding subcutaneous tissue 312. The fixation structures 302 preferably engage with the muscle tissue located along posterior surface 322 of the sacrum 324. In one embodiment the fixation structures 302 can be seen under fluoroscopy to allow the physician to verify that the fixation structures 302 are deployed. As shown in FIG. 5, the proximal portion 314 of the lead body 316 is bent and implanted through a subcutaneously tunneled path to the implantable pulse generator 12.

Figure 19:
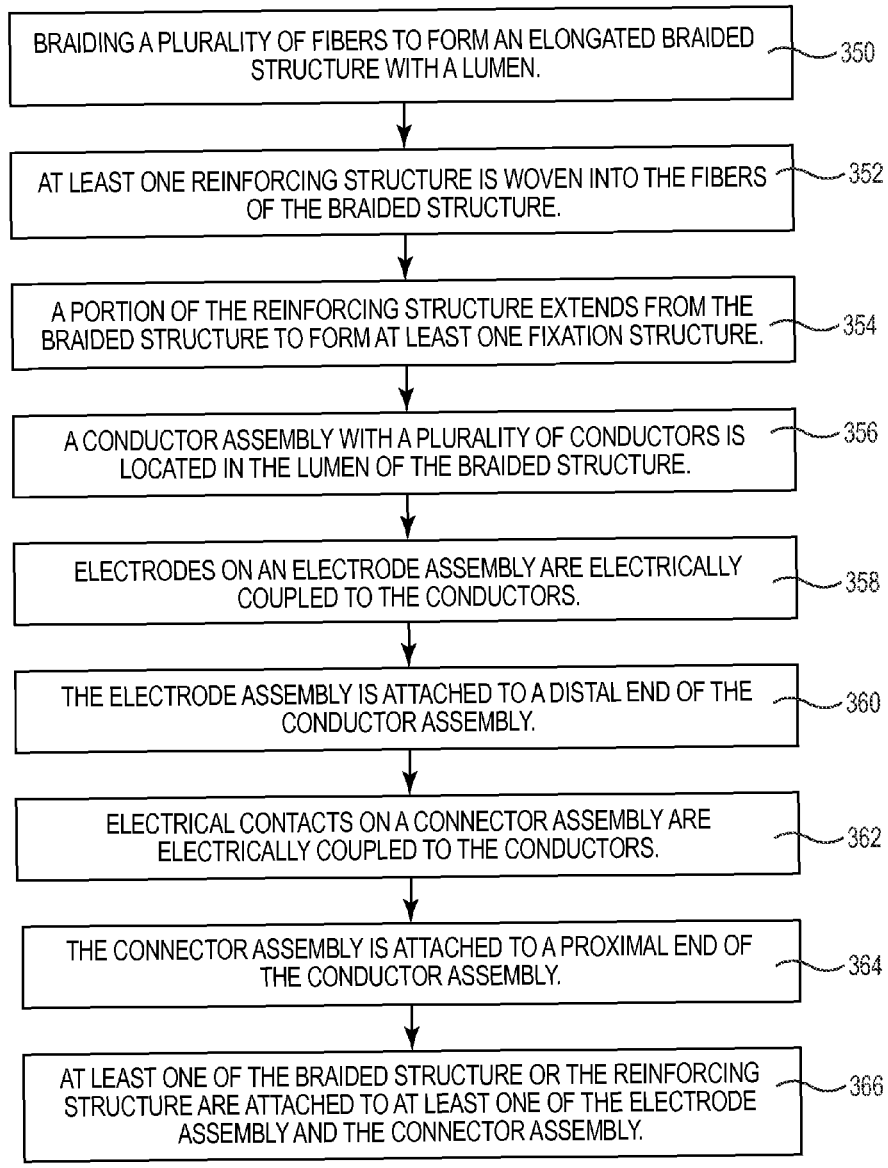
FIG. 19 is a flow chart of a method of making a therapy delivery element in accordance with an embodiment of the present disclosure.

FIG. 19 is a flow chart directed to a method of making a therapy delivery element configured for at least partial insertion in a living body according to an embodiment of the present disclosure. The method includes braiding a plurality of fibers to form an elongated braided structure with a lumen (350). At least one reinforcing structure is woven into the fibers of the braided structure (352). A portion of the reinforcing structure extends from the braided structure to form at least one fixation structure (354). A conductor assembly with a plurality of conductors is located in the lumen of the braided structure (356). Electrodes on an electrode assembly are electrically coupled to the conductors (358). The electrode assembly is attached to a distal end of the conductor assembly (360). Electrical contacts on a connector assembly are electrically coupled to the conductors (362). The connector assembly is attached to a proximal end of the conductor assembly (364). At least one of the braided structure or the reinforcing structure is attached to at least one of the electrode assembly and the connector assembly (366).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A therapy delivery element configured for at least partial insertion in a living body, the therapy delivery element comprising:
   a plurality of fibers braided to form an elongated braided structure having a lumen;
   at least one reinforcing structure woven into the fibers of the braided structure;
   at least one fixation structure integrally formed with and extending distally from the at least one reinforcing structure, the at least one fixation structure terminating at a free-floating distal end, wherein:
      in a deployed position, the at least one fixation structure extends generally radially outwardly from a central axis of the braided structure so that the distal end of the at least one fixation structure is spaced from the braided structure; and in a collapsed position, the at least one fixation structure extends generally longitudinally along the braided structure so that the distal end of the at least one fixation structure is disposed proximate the braided structure;

a conductor assembly comprising a plurality of conductors located in the lumen;

an electrode assembly located at a distal end of the conductor assembly, the electrode assembly comprising a plurality of electrodes electrically coupled to the conductors; and a connector assembly located at a proximal end of the conductor assembly, the connector assembly comprising a plurality of electrical contacts electrically coupled to the conductors, wherein at least one of the braided structure or the reinforcing structure is attached to at least one of the electrode assembly or the connector assembly.

2. The therapy delivery element of claim 1, wherein the braided structure is attached to both the electrode assembly and the connector assembly.

3. The therapy delivery element of claim 1, wherein the reinforcing structure is attached to at least the connector assembly.

4. The therapy delivery element of claim 1, wherein the at least one reinforcing structure is axially oriented and extends along substantially an entire length of the braided structure.

5. The therapy delivery element of claim 1, comprising a tubular structure surrounding the braided structure.

6. The therapy delivery element of claim 1, comprising a thermoplastic material melted into engagement with the braided structure.

7. The therapy delivery element of claim 1, wherein the at least one reinforcing structure is bonded to the braided structure.

8. The therapy delivery element of claim 1, wherein the at least one fixation structure includes a distal portion of the at least one reinforcing structure, a proximal portion of the at least one reinforcing structure being woven into the fibers of the braided structure, and the distal portion of the at least one reinforcing structure being removed from the fibers of the braided structure.

9. The therapy delivery element of claim 1, comprising:
a plurality of reinforcing structures each including a proximal portion woven into the fibers of the braided structure; and
a plurality of fixation structures including a distal portion of each of the plurality of the reinforcing structures being removed from the braided structure.

10. The therapy delivery element of claim 9, wherein the braided structure includes at least one reinforcing structure located along an entire length of the braided structure.

11. The therapy delivery element of claim 1, wherein the fixation structure comprises a shape configured to fold against the therapy delivery element during removal of the therapy delivery element from the living body.

12. The therapy delivery element of claim 1, comprising a plurality of fixation structures radially spaced around the elongated braided structure.

13. The therapy delivery element of claim 1, comprising a plurality of fixation structures axially offset along the elongated braided structure.

14. The therapy delivery element of claim 1, wherein the braided structure is configured to increase tensile strength of the therapy delivery element by at least 15%.

15. The therapy delivery element of claim 1, wherein the at least one fixation structure includes a length of at least 0.050 inches.

16. A neurostimulation system comprising:
an implantable pulse generator; and
a therapy delivery element comprising:
a plurality of fibers braided to form an elongated braided structure with a lumen;
at least one reinforcing structure woven into the fibers of the braided structure;
at least one fixation structure integrally formed with and extending distally from the at least one reinforcing structure, the at least one fixation structure terminating at a free-floating distal end, wherein:
in a deployed position, the at least one fixation structure extends generally radially outwardly from a central axis of the braided structure so that the distal end of the at least one fixation structure is spaced from the braided structure; and
in a collapsed position, the at least one fixation structure extends generally longitudinally along the braided structure so that the distal end of the at least one fixation structure is disposed proximate the braided structure;
a conductor assembly comprising a plurality of conductors located in the lumen;
an electrode assembly located at a distal end of the conductor assembly, the electrode assembly comprising a plurality of electrodes that are electrically coupled to the conductors; and
a connector assembly located at a proximal end of the conductor assembly, the connector assembly comprising a plurality of electrical contacts that are electrically coupled to the conductors and are configured to electrically couple with the implantable pulse generator, wherein at least one of the braided structure or the reinforcing structure is attached to at least one of the electrode assembly or the connector assembly.

17. The neurostimulation system of claim 16, wherein the at least one fixation structure includes a distal portion of the at least one reinforcing structure, wherein the distal portion extends from the braided structure with at least a proximal portion of the at least one reinforcing structure being woven into the fibers of the braided structure.

18. The neurostimulation system of claim 16, wherein the at least one reinforcing structure is bonded to the braided structure.

19. A therapy delivery element configured for at least partial insertion in a living body, the therapy delivery element comprising:
a plurality of fibers braided together to form an elongated substantially tubular braided structure including a lumen;
at least one reinforcing structure attached to the braided structure, a distal portion of the at least one reinforcing structure forming at least one fixation structure, the at least one fixation structure being integrally formed with and extending distally from the at least one reinforcing structure, the at least one fixation structure terminating at a free-floating distal end, wherein:
in a deployed position, the at least one fixation structure extends generally radially outwardly from a central axis of the braided structure so that the distal end of the at least one fixation structure is spaced from the braided structure; and
in a collapsed position, the at least one fixation structure extends generally longitudinally along the braided structure so that the distal end of the at least one fixation structure is disposed proximate the braided structure;

a conductor assembly disposed within the lumen, the conductor assembly including at least one conductor; and an electrode assembly located at a distal end of the conductor assembly, the electrode assembly including at least one electrode electrically coupled to the at least one conductor.

20. The therapy delivery element of claim 19, wherein at least a proximal portion of the at least one reinforcing structure is woven into the fibers of the braided structure.

21. The therapy delivery element of claim 19, wherein the at least one reinforcing structure is bonded to the braided structure.

22. The therapy delivery element of claim 19, comprising a plurality of fixation structures radially spaced around the braided structure.

* * * * *